(12) United States Patent
Ryan et al.

(10) Patent No.: US 7,390,663 B2
(45) Date of Patent: Jun. 24, 2008

(54) PROCESS, COMPOSITION AND KIT FOR PROVIDING A STABLE WHOLE BLOOD CALIBRATOR/CONTROL

(75) Inventors: Wayne L. Ryan, Omaha, NE (US); Bradford A. Hunsley, LaVista, NE (US)

(73) Assignee: Streck, Inc., LaVista, NE (US)

( * ) Notice: Subject to any disclaimer, the term of this patent is extended or adjusted under 35 U.S.C. 154(b) by 14 days.

(21) Appl. No.: 11/362,362

(22) Filed: Feb. 23, 2006

(65) Prior Publication Data
US 2006/0211072 A1 Sep. 21, 2006

Related U.S. Application Data

(60) Provisional application No. 60/656,154, filed on Feb. 23, 2005.

(51) Int. Cl.
*G01N 31/00* (2006.01)
*G01N 33/48* (2006.01)

(52) U.S. Cl. ................. 436/14; 436/8; 436/16; 436/18; 436/63; 436/95; 436/174; 436/176; 435/2; 435/14

(58) Field of Classification Search ........ 436/8, 436/10, 14, 16, 18, 63, 95, 174, 176; 435/2, 435/14
See application file for complete search history.

(56) References Cited

U.S. PATENT DOCUMENTS

| | | | |
|---|---|---|---|
| 4,358,394 A * | 11/1982 | Crews et al. ............ 436/10 |
| 4,489,162 A | 12/1984 | Hawkins et al. | |
| 4,579,824 A | 4/1986 | Louderback et al. | |
| 4,729,959 A * | 3/1988 | Ryan ..................... | 436/14 |
| 4,777,139 A | 10/1988 | Wong et al. | |
| 4,780,419 A | 10/1988 | Uchida et al. | |
| 5,028,542 A * | 7/1991 | Kennamer et al. ....... | 436/14 |
| 5,204,267 A * | 4/1993 | Sangha et al. .......... | 436/14 |
| 5,605,837 A * | 2/1997 | Karimi et al. .......... | 436/14 |
| 5,955,371 A | 9/1999 | Ikeda et al. | |
| 6,569,682 B2 | 5/2003 | Elliott et al. | |
| 6,632,844 B1 * | 10/2003 | Landt ................... | 514/693 |

FOREIGN PATENT DOCUMENTS

WO 03/069344 8/2003

OTHER PUBLICATIONS

Tang et al. Arch. Pathol. Lab. Med., vol. 124, Aug. 2000, pp. 1135-1140.*
Landt. Clinical Chemistry, vol. 46:8, 2000, pp. 1144-1149.*
le Roux et al. (abstract) Ann. Clincal Biochemistry, vol. 41(1):43-46, Jan. 2004.*

* cited by examiner

*Primary Examiner*—Maureen M Wallenhorst
(74) *Attorney, Agent, or Firm*—McHale & Slavin, P.A.

(57) ABSTRACT

The present invention is directed toward a stable calibrator and/or control, kit and process for using in a glucose monitoring instrumentation. Principally, the instant invention teaches a glycolyzed red blood cell component which has been treated with a glycolysis stabilizing effective amount of at least one non-crosslinking aldehyde compound which may be added to fresh plasma along with an amount of glucose to form a simulated whole blood glucose control product, effective for maintaining a particular and essentially stable glucose concentration over a period of time sufficient for accurate measurement and calibration of a glucose measuring instrument.

32 Claims, 9 Drawing Sheets

FIGURE 2

Comparison of Glucose Recovery from Whole Blood and Whole Blood
Treated with Glyceraldehyde with POC Blood Glucose Meters Glucose Concentration mg/dl

| Sample | Lifescan Ultra | Lifescan One Touch | Lifescan SureStep | Advantage S.Comfort | Glucometer Elite | MediSense Precision PCx | YSI* |
|---|---|---|---|---|---|---|---|
| Whole Blood <br> Low Level Glucose | | | | | | | |
| Mean: | 60.2 | 67.2 | 73.2 | 74.0 | 58.0 | 74.0 | 67 |
| S.D.: | 1.47 | 1.57 | 3.24 | 2.45 | 1.15 | 1.29 | |
| C.V.: | 2.45 | 2.34 | 4.42 | 3.31 | 1.99 | 1.74 | |
| % Recovery | 89.8 | 100.2 | 109.2 | 110.4 | 86.6 | 110.4 | |
| Whole blood with 10 mM glyceraldehyde <br> Low Level Glucose | | | | | | | |
| Mean: | 72.3 | 76.3 | 85.8 | 88.0 | 70.7 | 84.2 | 78 |
| S.D.: | 2.73 | 2.36 | 2.73 | 5.42 | 1.97 | 1.86 | |
| C.V.: | 3.78 | 3.09 | 3.18 | 6.15 | 2.79 | 2.21 | |
| % Recovery | 92.7 | 97.9 | 110.0 | 112.8 | 90.6 | 107.9 | |
| Whole Blood <br> Mid Level Glucose | | | | | | | |
| Mean: | 201.3 | 184.8 | 198.7 | 200.8 | 206.8 | 189.2 | 185 |
| S.D.: | 3.64 | 3.13 | 2.21 | 4.74 | 4.84 | 3.89 | |
| C.V.: | 1.81 | 1.69 | 1.11 | 2.36 | 2.34 | 2.06 | |
| % Recovery | 108.8 | 99.9 | 107.4 | 108.6 | 111.8 | 102.3 | |
| Whole Blood with 10mM Glyceraldehyde <br> Mid Level Glucose | | | | | | | |
| Mean: | 209.5 | 191.2 | 203.2 | 211.0 | 209.0 | 197.5 | 194 |
| S.D.: | 3.30 | 4.02 | 3.58 | 5.77 | 3.92 | 5.80 | |
| C.V.: | 1.58 | 2.10 | 1.76 | 2.74 | 1.87 | 2.93 | |
| % Recovery | 108.0 | 98.5 | 104.7 | 108.8 | 107.7 | 101.8 | |
| Whole Blood <br> Elevated Glucose Level | | | | | | | |
| Mean: | 318.0 | 286.0 | 327.3 | 350.2 | 321.7 | 287.7 | 298 |
| S.D.: | 2.77 | 7.51 | 5.47 | 9.44 | 9.99 | 5.71 | |
| C.V.: | 0.87 | 2.62 | 1.67 | 2.70 | 3.11 | 1.98 | |
| % Recovery | 106.7 | 96.0 | 109.8 | 117.5 | 107.9 | 96.5 | |
| Whole Blood with 10mM Glyceraldehyde <br> Elevated Glucose Level | | | | | | | |
| Mean: | 339.8 | 303.2 | 350.2 | 376.8 | 344.5 | 307.3 | 322 |
| S.D.: | 3.58 | 6.91 | 5.15 | 12.28 | 7.09 | 12.27 | |
| C.V.: | 1.05 | 2.28 | 1.47 | 3.26 | 2.06 | 3.99 | |
| % Recovery | 105.5 | 94.2 | 108.7 | 117.0 | 107.0 | 95.4 | |

Whole Blood was collected in K3EDTA with and without Glyceraldehyde 10mM.
Mean value is derived from 6 results measured on two meters of each type.
% Recovery is derived by comparing the recovered value with that from the YSI 2300 STAT*
Glucose Reference Method.

FIGURE 3A

| Instrument | | Whole Blood YSI* = 50 mg/dl | | Glucose & Water YSI = 50 mg/dl | |
|---|---|---|---|---|---|
| | | Mean | Accuracy% | Mean | Accuracy% |
| Instrument A | Strip Lot # 1 | 51.1 | | 81 | |
| | Strip Lot # 2 | 48.3 | | 84.6 | |
| | Strip Lot # 3 | 47 | | 99 | |
| | MEAN | 48.8 | -2% | 88 | +76% |
| | C.V. | 4.60% | | 14% | |
| Instrument B | Strip Lot # 1 | 48 | | 58.8 | |
| | Strip Lot # 2 | 50.1 | | 58.8 | |
| | Strip Lot # 3 | 50.9 | | 60.3 | |
| | MEAN | 49.7 | 0% | 59.3 | +19% |
| | C.V. | 4.90% | | 6.80% | |
| Instrument C | Strip Lot # 1 | 43.6 | | 61 | |
| | Strip Lot # 2 | 44.4 | | 58.1 | |
| | Strip Lot # 3 | 42.8 | | 59.6 | |
| | MEAN | 43.6 | -13% | 59.6 | +19% |
| | C.V. | 4.60% | | 6.10% | |
| Instrument D | Strip Lot # 1 | 49.7 | | 37.9 | |
| | Strip Lot # 2 | 43.9 | | 38.3 | |
| | Strip Lot # 3 | 43.7 | | 37.2 | |
| | MEAN | 45.7 | -9% | 37.8 | -24% |
| | C.V. | 7.30% | | 6.60% | |
| Instrument E | Strip Lot # 1 | 49.9 | | 32.2 | |
| | Strip Lot # 2 | 48.6 | | 34.2 | |
| | Strip Lot # 3 | 49 | | 32.2 | |
| | MEAN | 49.1 | -4% | 32.9 | -34% |
| | C.V. | 4.40% | | 8.40% | |

FIGURE 3B

| Instrument | | Whole Blood *YSI = 150 mg/dl | | Glucose & Water *YSI = 150 mg/dl | |
|---|---|---|---|---|---|
| | | Mean | Accuracy% | Mean | Accuracy% |
| Instrument A | Strip Lot # 1 | 159.1 | | 172.4 | |
| | Strip Lot # 2 | 151.4 | | 171.8 | |
| | Strip Lot # 3 | 152.3 | | 178.2 | |
| | MEAN | 154.3 | 3% | 172.4 | 15% |
| | C.V. | 3.10% | | 8.80% | |
| Instrument B | Strip Lot # 1 | 144.3 | | 94.3 | |
| | Strip Lot # 2 | 139.3 | | 96.4 | |
| | Strip Lot # 3 | 142 | | 100 | |
| | MEAN | 141.9 | -5% | 96.9 | -35% |
| | C.V. | 3.40% | | 7.50% | |
| Instrument C | Strip Lot # 1 | 136.8 | | 87 | |
| | Strip Lot # 2 | 134 | | 91.8 | |
| | Strip Lot # 3 | 136.4 | | 96.3 | |
| | MEAN | 135.7 | -10% | 91.7 | -39% |
| | C.V. | 3.10% | | 9.30% | |
| Instrument D | Strip Lot # 1 | 130.3 | | 150.3 | |
| | Strip Lot # 2 | 129.7 | | 152.3 | |
| | Strip Lot # 3 | 125 | | 149.7 | |
| | MEAN | 128.3 | -14% | 150.8 | 1% |
| | C.V | 3.30% | | 4.20% | |
| Instrument E | Strip Lot # 1 | 135.1 | | 122.8 | |
| | Strip Lot # 2 | 138.8 | | 118.6 | |
| | Strip Lot # 3 | 153 | | 122.1 | |
| | MEAN | 142.3 | -5% | 121.1 | -19% |
| | C.V. | 6% | | 4.80% | |

FIGURE 3C

Variability in Recovery of Glucose on POC Glucose Monitors from Commercial Control Products

Commercial Control 1

|  |  | YSI* = 50 mg/dl | | | *YSI = 150 mg/dl | |
|---|---|---|---|---|---|---|
| LEVEL 1 |  | Mean | Accuracy % | LEVEL 2 | Mean | Accuracy % |
| Instrument A | Strip Lot # 1 | 57.7 |  |  | 166.2 |  |
|  | Strip Lot # 2 | 57 |  |  | 178.9 |  |
|  | Strip Lot # 3 | 58.1 |  |  | 173.4 |  |
|  | MEAN | 57.6 | 15% |  | 172.9 | 15% |
|  | C.V. | 4.60% |  |  | 3.90% |  |
| Instrument B | Strip Lot # 1 | 59.2 |  |  | 174.9 |  |
|  | Strip Lot # 2 | 57.1 |  |  | 174.2 |  |
|  | Strip Lot # 3 | 56.1 |  |  | 167.2 |  |
|  | MEAN | 57.5 | 15% |  | 172.2 | 15% |
|  | C.V. | 5.30% |  |  | 3.60% |  |
| Instrument C | Strip Lot # 1 | 61.5 |  |  | 189.7 |  |
|  | Strip Lot # 2 | 59.7 |  |  | 185.9 |  |
|  | Strip Lot # 3 | 62.1 |  |  | 180.8 |  |
|  | MEAN | 61.1 | 22% |  | 185.5 | 23% |
|  | C.V. | 4.90% |  |  | 3.60% |  |
| Instrument D | Strip Lot # 1 | 48.1 |  |  | 147.3 |  |
|  | Strip Lot # 2 | 43.6 |  |  | 144 |  |
|  | Strip Lot # 3 | 49.3 |  |  | 154.9 |  |
|  | MEAN | 47 | -6% |  | 148.7 | -1% |
|  | C.V. | 7.10% |  |  | 4.40% |  |
| Instrument E | Strip Lot # 1 | 51.3 |  |  | 151.1 |  |
|  | Strip Lot # 2 | 51.2 |  |  | 144.9 |  |
|  | Strip Lot # 3 | 47.7 |  |  | 157.6 |  |
|  | MEAN | 50.1 | 0% |  | 151.2 | 1% |
|  | C.V. | 5.70% |  |  | 4.60% |  |

FIGURE 3D

Commercial Control 2

| | | LEVEL 1 | YSI = 40 mg/dl | | LEVEL 2 | YSI = 205 mg/dl | |
|---|---|---|---|---|---|---|---|
| | | Mean | Accuracy % | | Mean | Accuracy % | |
| Instrument B | Strip Lot # 1 | 50.7 | | | 312.7 | | |
| | Strip Lot # 2 | 48.6 | | | 311.6 | | |
| | Strip Lot # 3 | 52.7 | | | 281.1 | | |
| | MEAN | 50.6 | +27% | | 301.8 | +47% | |
| | *C.V.* | *7.10%* | | | *5.50%* | | |
| Instrument C | Strip Lot # 1 | 56.2 | | | 326.4 | | |
| | Strip Lot # 2 | 55.3 | | | 322.2 | | |
| | Strip Lot # 3 | 57 | | | 293.3 | | |
| | MEAN | 56.2 | +41% | | 314 | +53% | |
| | *C.V.* | *7.10%* | | | *5.50%* | | |
| Instrument F | Strip Lot # 1 | 57 | | | 316.6 | | |
| | Strip Lot # 2 | 54.4 | | | 305.7 | | |
| | Strip Lot # 3 | 57.6 | | | 281.2 | | |
| | MEAN | 56.3 | +41% | | 301.1 | +47% | |
| | *C.V.* | *7.10%* | | | *5.70%* | | |

US 7,390,663 B2

PROCESS, COMPOSITION AND KIT FOR PROVIDING A STABLE WHOLE BLOOD CALIBRATOR/CONTROL

REFERENCE TO RELATED APPLICATIONS

This application claims benefit of the filing date of Provisional Application 60/656,154, filed on Feb. 23, 2005, the contents of which is herein incorporated by reference.

FIELD OF THE INVENTION

This invention generally relates to a process, composition and kit for providing a stable whole blood calibrator and/or control for use in analyte measuring systems. The invention particularly relates to the addition of a non-cross linking aldehyde to glucose depleted whole blood or red blood cells and to the production of glucose stable aliquots therefrom having varying concentrations of glucose; and most particularly to the use of glyceraldehyde to stabilize glucose metabolism in red blood cells to create a calibrator and/or control to enable precise long-term monitoring and calibration of blood glucose monitoring instruments.

BACKGROUND OF THE INVENTION

There are numerous commercially available systems and/or devices for diagnostic testing of analytes in tissue samples. Currently, a growing number of manufacturers sell single-use lateral flow devices, or test strips, for glucose monitoring. These test strips are part of a segment of in vitro diagnostics called Point-of-Care (POC) devices. Test strips are typically read by either reflectance or electrochemical POC measurement systems.

Reflectant-based glucose strips are composed of three distinct layers; an absorbent pad, a reagent-impregnated membrane, and an enzymatic membrane. Reflectance photometric systems quantitate glucose concentrations by measuring the amount of light reflected from the reagent membrane surface.

Electrochemical systems utilize amperometry or coulometry to quantitate glucose amounts. For amperometric systems, a constant potential is applied to the electrodes and the current flowing through the electrochemical cell is measured. For coulometric systems, the amount of electricity passing between the electrodes is proportional to the quantity of substance manufactured or used by the reduction-oxidation process. In order for POC devices to achieve glucose agreement with central laboratory analyzers, it is often necessary to employ a whole blood control or one that provides close mimicry to whole blood.

Unlike remotely located central laboratories, POC measurement devices provide immediate analyte concentration. These test strips are designed to accept and test whole blood specimens for immediate results. Often such instantaneous glucose level determination is vital for proper diabetes management.

In contrast to POC devices, the methods and "wet" chemistry analyzers used by central laboratories are often less sensitive than POC systems to the "matrix" of the specimen. A "matrix-effect" results when other constituents of a sample besides the analyte tested for produce a matrix shift, or a measurement bias, thereby reducing the accuracy of the analyzer to correctly measure the analyte concentration. Matrix-effects caused by the interaction of processed material and the analytical system may generate an underestimation, or overestimation, of true glucose levels leading to possible misdiagnosis in the patient.

Thus, matrix effects are especially troublesome with Quality Control and Proficiency Testing materials as well as for POC glucose strip manufacturers. The matrix-effect makes it extremely difficult to achieve agreement between the various POC glucose strip systems using a stabilized blood material. Test strips are made by a complicated process of assembling different laminates and/or substrates for removal of cellular components, red blood cells (RBCs) or erythrocytes, enzymes for metabolizing the analyte and reagents to signal a reaction detecting the presence or absence of analyte. By the very nature of the process, significant lot-to-lot variability can occur.

Currently, providers of Glucose Measurement Proficiency Programs must use stabilized materials that exhibit significant matrix effects. The administrators of these programs thus find it necessary to separate the reported results according to the make and model of the glucose monitoring devices. Ideally, the proficiency material should mimic fresh blood so that a single assay value could be used to evaluate the performance of all systems.

POC glucose test strip/instrument manufacturers have a problem in that each lot or batch of strips can differ from others in response to glucose. Variations in manufacturing conditions and materials accounts for this difference. To account for the variations in response, calibration codes are assigned to each strip lot number. Currently, fresh blood samples are used for this assignment. Due to the rapid deterioration of the blood samples, often the only relatively reliable calibrator and/or control is fresh human blood, frequently obtained from POC strip manufacture employees themselves. Precise control of the glucose level is especially difficult since the RBCs in whole blood continue to metabolize. If left at room temperature, the collected blood samples undergo glycolysis. That is, glycolytic enzymes in blood convert the glucose to pyruvic acid and other products by a series of reactions known as the Embden-Meyerhof pathway. To prepare this calibrator, blood is drawn into an anticoagulant to form a suspension. The suspension is then incubated for a few hours to reduce the glucose level, preferably to 50 mg/dL or less. Glucose is then added to achieve the various levels desired for calibration. To maintain the glucose level for future use as a calibrator and/or control, the blood must be immediately stored on ice. While this method can reduce glycolysis, long-term storage on ice can eventually degrade the sample.

Other methods and procedures have been described in the prior art for preparing stable controls and/or calibrators, especially in glucose monitoring instrumentation. One such method has been to immediately completely remove RBCs from fresh whole blood by centrifugation. Since RBCs can comprise up to 50% of the whole blood, the remaining primary components, mainly plasma, do not adequately mimic whole blood in analytical systems. The RBC component contributes to the viscosity, ionic strength and absorption. Because there is failure to achieve total accordance, matrix-effects result.

In glucose lateral flow devices, the presence of the RBCs in the whole blood affects the regulation of sample flow through the various strip layers. That is, the RBCs physically fill and/or plug the pores of the reagent membrane, thus regulating the flow dynamics to the subsequent layer. Moreover, the ionic strength of the RBCs impacts reaction kinetics that in turns shortens, or extends, the reaction phase (i.e. impact slope and time to reach endpoint).

Therefore, in the absence of either the RBCs or ionic strength, sample migration through the test strip layers is markedly different. Rate of absorption, sample delivery through the reagent membrane and flow rate of the enzymatic reaction is changed. Hence, the creation of a stable, control solution that closely simulates cellular components, function characteristics (i.e. size, density, charge and concentration) while operating universally across different POC glucose monitoring devices and maintaining agreement with results obtained from a central laboratory has been heretofore lacking in the prior art.

In accordance with the instantly disclosed invention, a glucose control will be understood to comprise a stable suspension of red cells and plasma, or components which may be combined to produce said stable suspension, that can be analyzed for glucose over a time period of several weeks, with recovery of a consistent value.

In the past various glycolytic inhibitors have been utilized in blood samples to inhibit glycolysis in a sample before the sample is tested. Some common inhibitors include, sodium fluoride, sodium iodoacetate, sodium oxalate, 2-iodoacetamide, d-mannose, either alone or in combination with an anticoagulant. Although these inhibitors will stabilize the glucose in blood specimens, they are usually identified as "incompatible" and/or "interfering" substances when used in combination with many commercially available POC glucose monitors. Therefore, although they inhibit glucose metabolism they do not provide an acceptable control material. Furthermore, it often takes approximately three hours for these glycolytic inhibitors to become fully effective and stabilize glucose levels. During this three-hour lag time, approximately 0.5 mmol/L of glucose can be consumed.

Some cross-linking aldehydes, for example formaldehyde and glutaraldehyde, have been employed to inhibit glycolysis in blood samples. These aldehydes "cross-link" with cellular surface proteins and amino acids. For the purposes of calibration, cross-linking of cellular membrane proteins is not desirable since the characteristics of the whole blood (RBC) would be changed and possibly impact the behavior of the various glucose monitoring systems. While, glyceraldehyde does react with some amino acids to form Schiff bases, it does not "cross-link" with cellular surface proteins. That is, it is monofunctional. In addition, it is rapidly transported through the red blood cell membranes to quickly inhibit glycolysis.

Thus, it has been discovered by the present inventors that not only does the use of non-cross linking aldehydes stabilize glucose values by inhibiting the glycolytic process, but these aldehydes do not affect the rheology (i.e. flow properties) of the RBCs through testing devices. Therefore, it is possible to make a calibrator comprising at least one non-cross linking aldehyde for calibration with the various methodologies ranging from the analyzer in the central laboratory to the POC monitor.

DESCRIPTION OF PRIOR ART

Many studies, articles and patents have been directed toward the use of various methods and compositions to preserve blood samples, particularly to stabilizing the initial level of glucose in whole blood for later analytic testing.

For example, U.S. Pat. No. 6,632,844, to Landt, (the contents of which are herein incorporated by reference), teaches a method for preserving and/or stabilizing glucose levels of a whole blood sample using glyceraldehydes, wherein the final concentration of glyceraldehyde in the blood sample is preferably between about 0.9 to 20 mM. This allows for the transport of the stabilized sample to a centralized laboratory for testing within 16 hours with negligible glucose loss.

In contrast to that which is disclosed in the Landt reference, the present invention forms a control and/or calibrator for use in glucose measuring systems through the creation of aliquots of glucose at different concentrations. What is particularly unique is that subsequent to obtaining the blood sample, the initial concentration of glucose is allowed to undergo glycolysis until the glucose is at a predetermined concentration, at which time the RBC are separated and treated with a non-cross linking aldehyde to stop further glycolysis.

WIPO Publication No. 2003/069344 A1 to Le Roux et al., (herein incorporated by reference) disclose a composition useful for inhibiting glycolysis in tissue samples, such as blood. The composition includes glyceraldehyde, or mimetic thereof; a glycolytic inhibitor; and an anticoagulating agent. Le Roux et al., teaches the combination of glyceraldehyde with a composition having a high anti-glycolytic activity. The anti-glycolytic activity is achieved through the use of an additional glycolytic inhibitor and anti-coagulating agent to stabilize glucose levels more effectively than the addition of 0.9 to 20 mM of glyceraldehyde alone, as taught by Landt (U.S. Pat. No. 6,632,844). This is counterintuitive to the present invention, which does not initially halt the blood sample from undergoing glycolysis.

U.S. Pat. No. 4,780,419 to Uchida et al., (herein incorporated by reference), teach a method for reducing glycolysis by adding citric acid, malonic acid and/or maleic acid to blood-collection tubes such that the resulting pH of the blood sample is between 5.0 to 7.0. Moreover, the method of preserving can include an additional glycolytic inhibitor, preferably sodium fluoride (NaF), to further decrease glycolysis. Sodium fluoride is associated with antiglycolytic action as well as hemolytic toxicity and anticoagulant activity.

U.S. Pat. No. 5,955,371 to Ikeda et al., herein incorporated by reference, disclose a VACUTAINER® tube containing a powder comprising sodium fluoride and ethylene diamine tetraacetic acid (EDTA). The particle size of the NaF and EDTA powder provides an improved additive fill due to the consistency of the particle components. The use of granulated particles thereby decreases false data generated by instrumentation for the measurement of glucose by reducing the overall variation in fill quantities.

U.S. Pat. No. 4,777,139 is directed toward a hematology control of enhanced stability wherein red cells are exposed to an unsaturated aldehyde such as acrolein (propenal) under conditions sufficient to increase the stability of the cells without impairing the ability of a lysing reagent to lyse the cells. After treatment, the treated cells are washed and are suspended in a stabilizing suspension medium, whereby stable MCV values result. The '139 patent fails to teach or disclose stabilization of glucose levels by addition of glyceraldehyde or an equivalent non-cross linking aldehyde, to a glucose depleted sample, in amounts effective to result in a glucose stable whole blood control composition which remains stable over extended periods of time.

U.S. Pat. No. 4,579,824 discloses a hematology control which is useful for clinical hematology procedures and, in particular, mean corpuscular volume (MCV) determinations. The hematology control comprises an aqueous suspension of red blood cells in which varying levels of MCV are provided by applying to the red cell component, after light treatment with aldehyde, an osmotic pressure that is directly proportional to the desired red blood cell size. The '824 patent fails to teach or disclose stabilization of glucose levels by addition of glyceraldehyde or an equivalent non-cross linking aldehyde, to a glucose depleted sample, in amounts effective to result in a glucose stable whole blood control composition which remains stable over extended periods of time.

U.S. Pat. No. 4,489,162 teaches a hematologic control and calibration standards which are essentially plasma-free.

These controls are prepared by the suspension of red blood cells in an appropriate buffer containing a stabilization effective amount of disaccharides, and other optional ingredients. Control and calibration standards prepared in the foregoing manner are suitable in the control and calibration of hematology analyzers for the following parameters: white cell count, red cell count, hemoglobin, hematocrit and the common derived parameters (i.e., mean cell volume, mean cell hemoglobin and mean cell hemoglobin concentration). The addition of platelets to the foregoing suspensions is also contemplated to provide a control for platelet parameters.

U.S. Pat. No. 6,569,682—teaches an improved blood suspension media for hematological compositions, having particular utility with a red blood cell component for devices using electronic and optical means for blood determinations, and processes for using the suspension media. The suspension media finds particular utility in providing the hematology control product with a stable and consistent MCV and RDW for an extended product shelf life.

In contrast to that which is disclosed in the prior art, the present invention allows the fresh blood sample to initially undergo glycolysis to a predetermined level, the cellular component is then separated from the plasma and exposed to at least one non-crosslinking aldehyde to stabilize the glucose level. A separated plasma is added back to the stabilized cellular component for the purpose of providing a whole blood glucose control or proficiency material, which can be used for at least 1 month.

SUMMARY OF THE INVENTION

The instant process illustrates a simple and elegant procedure to produce a glucose stable whole blood control composition useful over extended periods of time as a calibrator for point-of-care (POC) glucose monitors, and the like. In one embodiment the method provides a procedure to separate and treat the cellular components, i.e. RBCs, with an appropriate non-cross linking aldehyde for providing glucose stable RBC's suitable for inclusion in plasma, whereby a glucose stable calibrator of enhanced quality is produced.

Accordingly, the principle object of the present invention is to provide a stable primary control and/or calibrator for use in glucose monitoring systems that is viable for an extended period of time.

It is an objective of the present invention to prepare a control/calibrator that would show less than about a 3% difference between a "true" value obtained on a central laboratory analyzer and that obtained on a POC glucose monitor.

A further objective of the instant invention provides manufacturers with a stable primary calibrator that reflects all the analytical nuances of whole blood such as ionic strength, viscosity, flow rate, etc, to closely emulate fresh whole blood on glucose monitoring devices, without suffering from the matrix effect related deficiencies of the prior art.

Yet another object of the present invention is to teach a glucose control composition and/or calibrator kit comprising at least one glycolyzed red blood cell component which has been treated with a glycolysis stabilizing effective amount of at least one non-crosslinking aldehyde compound, and at least one vessel fresh plasma resuspending material, whereby the components are combined to form a control and/or calibrator which can be adjusted to a particular and essentially stable desired glucose concentration.

It is a further objective of the present invention to provide a glycolyzed red blood cell component which has been treated with a glycolysis stabilizing effective amount of at least one non-crosslinking aldehyde compound; said red blood cell component effective for use in preparing a simulated whole blood stable glucose control composition effective to maintain a particular and essentially stable glucose concentration over a period of time sufficient for accurate measurement and calibration of a glucose measuring instrument.

The above described and many other features and attendant advantages of the present invention will become apparent as the invention becomes better understood by reference to the following detailed description when considered in conjunction with the accompanying drawings.

BRIEF DESCRIPTION OF DRAWINGS

FIG. 2 illustrates the absence of matrix effects across six different analyzers which utilize either electrochemical or reflectance technology; biases are shown in individual systems on whole blood matched with and without glyceraldehyde addition;

FIGS. 3A, 3B, 3C and 3D show values of percent accuracy collected using five different "major" market POC glucose monitors, and demonstrate variability in recovery of glucose on POC glucose monitors utilizing whole blood and aqueous glucose control solutions;

DETAILED DESCRIPTION

In its broadest sense, the blood source of the present invention will include both human and other animals. Without limiting the scope of the present invention, suitable blood sources include bovine, avian, porcine, equine, goat, alligator, etc.

Whole blood, as used herein refers to a suspension of red blood cells, white blood cells, plasma and platelets. Additionally, whole blood may also contain an anticoagulant.

While numerous anticoagulants are capable of functioning in accordance with the process of the instant invention, non-limiting illustrative examples of such anticoagulants include EDTA, heparin, citrate, and salts thereof, which are useful either alone or in combination.

Plasma, as used herein refers to non-cellular or proteinaceous portion, which can contribute up to about 55% of whole blood volume.

Red blood cells (RBCs), or erythrocytes, refer to the cellular or non-proteinaceous portion that can make up to about 40% to 50% of whole blood volume.

"Accuracy", as used herein refers to the relationship between the actual meter response and the "true" analyte concentration reported by the reference analyzer (YSI) and is measured in terms of percent recovery.

"Precision", or "CV %" as used herein refers to the measure of the control's reproducibility within and across multiple strip lots and shares no relationship to accuracy.

In accordance with the instantly disclosed invention, a "glucose control" or "glucose calibrator" will be understood to comprise a stable suspension of red cells and plasma, or components which may be combined to produce said stable suspension, that can be analyzed for glucose over a time period of several weeks, with recovery of a consistent value.

Without limiting the scope of the present invention, suitable non-cross linking aldehydes include, glyceraldehyde (otherwise known as 2,3-dihydroxypropanal, alpha, beta-dihydroxypropanal, glyceric aldehyde), glycolaldehyde, benzaldehyde, hydroxypyruvaldehyde, and acetaldehyde and racemic forms or combinations thereof known to one of ordinary skill. The most preferred non-cross linking aldehyde being D, or L-glyceraldehyde, with the L isomer form of glyceraldehyde most preferred.

Figure 1:
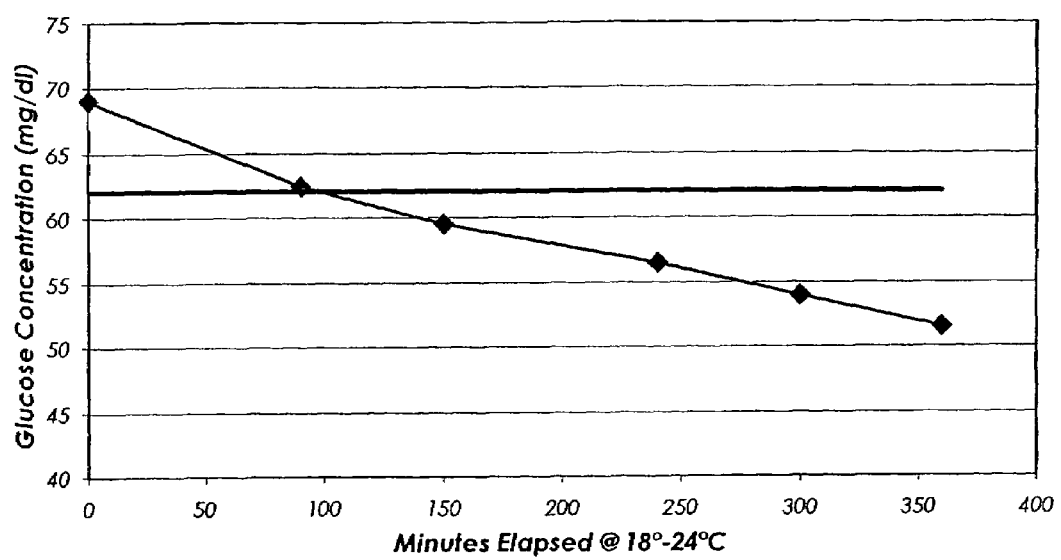
FIG. 1 evidences the inherent problem of glycolysis in fresh whole blood, whereby glucose concentrations quickly degrade over time subsequent to blood being drawn.

As illustrated in FIG. 1, there are inherent problems of glycolysis in fresh whole blood, whereby glucose concentrations quickly degrade over time subsequent to blood being drawn. Glucose data was collected on a YSI 2300 STAT device, and the decrease in glucose concentration was monitored with respect to time within a range of 18°-24° C. Glucose concentration decreased 10% within the first 90 minutes.

To closely replicate the functional characteristics of fresh whole blood, controls and/or calibrators should provide both accuracy and precision.

FIG. 2 illustrates the effect of the control of the instant invention across six of the largest commercial POC glucose monitors according to recent CAP survey. The instrumentation consisted of both electrochemical and reflectance type analyzers. A comparison of glucose recovery from whole blood and whole blood treated with glyceraldehyde on various POC blood glucose meters was carried out. The data illustrates fresh whole blood recoveries relative to YSI, performed with two meters from each selection in triplicate. The analysis was performed at three different concentrations of glucose (80 (low), 180 (Mid Level) and 300 (Elevated) mg/dL). The whole blood was collected in EDTA with and without a racemic mixture of D,L-glyceraldehyde at 10 mM for a period of about 4 hours. The percentages indicate a less than 3% difference between analyzed fresh whole blood with and without the non-cross linking aldehyde of the present invention. This is proof of principle that the inclusion of glucose stabilizing amounts of aldehyde, e.g. glyceraldehyde, does not contribute any significant matrix effect. The CV % value refers to the coefficient of variation of glucose controls.

Performance data in FIGS. 3A-3D were collected using five different "major" market POC glucose monitors. The data was collected across three different reagent test strip lots per instrument type at 18° C. to 20° C.

FIGS. 3A and 3B particularly illustrate the current deficiencies which exist as demonstrated by a comparative analysis between various samples: fresh whole blood and glucose in water. The glucose concentration was set at 50 mg/dL (FIG. 3A) and 150 mg/dL (FIG. 3B) on a single YSI 2300 STAT centralized analyzer, using a glucose reference method.

The values obtained with water and glucose were found to have 2 to 4× less precision than with fresh whole blood. Percent accuracy of glucose recoveries, relative to the YSI 2300 analyzer, are as follows:

FIG. 3A
Fresh Whole Blood: low of 87% and high of 100%;
Glucose in $H_2O$: low of 76% and high 176%.

FIG. 3B
Fresh Whole Blood: low of 86% and high of 103%
Glucose in $H_2O$: low of 61% and high of 115%

FIGS. 3C-3D illustrate comparative analyses of precision and accuracy between various commercial POC instruments using available commercial controls at varying glucose concentrations.

FIG. 3C utilizes an aqueous commercial control at 50 and 150 mg/Dl glucose samples: fresh whole blood control, commercial control (i.e. SUGAR CHEX available from Streck Laboratories, Inc.) glucose in water. All specimens contain 150 mg/dL glucose.

The values obtained with water and glucose were found to have 3 to 4× less precision than with fresh whole blood.

Percent accuracy of glucose recoveries, relative to YSI 2300 analyzer, are as follows:
50 mg/Dl
Commercial Control: low of 94% and high of 122%
150 mg/DL
Commercial Control: low of 99% and high of 123%

FIG. 3D illustrates performance data collected using a major commercially available POC glucose monitor in combination with Commercial Control 2, an aqueous glucose control. Data was collected in triplicate across three different meters across three reagent test strip lots per instrument type. The precision characteristics were found to be comparable to fresh whole blood. However, the glucose percent recoveries with respect to the YSI 2300 analyzer, range greatly from 127% to 153%. Again, the accuracy in this system is lacking.

Percent accuracy of glucose recoveries, relative to YSI 2300 analyzer, are as follows:
40 mg/Dl
Commercial Control: low of 127% and high of 141%
150 mg/DL
Commercial Control: low of 147% and high of 153%

Illustrative, albeit non-limiting, examples of methods to achieve the foregoing objects of the present invention are discussed herein.

EXAMPLE 1

In one method, a sample containing a cellular component, (i.e. RBCs, WBCs) is collected into a microfuge or vacuum tube, e.g. VACUTAINER®, (such as supplied by Becton, Dickinson and Company, Franklin Lakes, N.J.). The initial concentration of glucose in the sample can be 50 mg/mL to 110 mg/mL.

The vacuum tube may contain any appropriate anticoagulant agent known to one of ordinary skill, including oxalate, EDTA, citrate, heparin or combination thereof, to form a suspension. If used, the anticoagulant may be added together simultaneously, or sequentially, to the sample.

The resulting suspension is incubated at about 2° C. to about 30° C. and allowed to undergo glycolysis until the glucose level is less than about 20 mg/dL.

An anti-glycolytic inhibitor solution, preferably at least one non-cross linking aldehyde, most preferably glyceraldehyde, is added to the vacuum tube at concentrations of about 20 to 200 mM. In one illustrative embodiment, the anti-glycolytic inhibitor solution can include a mixture of any non-cross linking aldehydes or other anti-glycolytic components known in the art. Additionally, the anti-glycolytic inhibitor may include at least one buffer known in the art.

After a predetermined period of incubation, about 60 minutes, the final level of glucose is added at predetermined calibration levels to create standardized and stabilized aliquots of glucose. Preferably the final glucose concentration is adjusted to at least one predetermined concentration, from about 20 mg/L to about 1000 mg/L, for example, 50, 100, 200, 400 mg/dL. Alternative concentrations to calibrate glucose measuring devices obvious to one of ordinary skill in the art may be used. Preferably, the amount of glucose added produces less than 1% dilution of sample.

Figure 4:
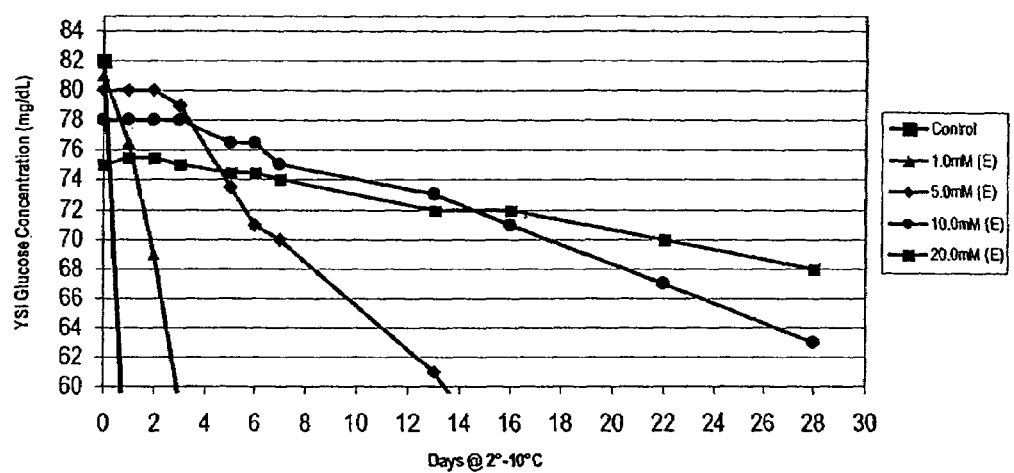
FIG. 4 illustrates the YSI glucose concentration (mg/dL) of blood specimens containing EDTA at various final concentrations of a mixture of D,L glyceraldehydes at 0.0, 1.0, 5.0, 10.0 and 20.0 mM, obtained over 4 weeks of real time testing at about 2° C. to about 10° C.

FIG. 4 illustrates the YSI glucose concentration (mg/dL) of blood specimen containing EDTA at various final concentrations of a mixture of D,L glyceraldehydes at 0.0, 1.0, 5.0, 10.0 and 20.0 mM, obtained over 4 weeks of real time testing at about 2° C. to about 10° C. It was discovered, the YSI glucose concentration was found to exhibit less than 10% loss at 4 weeks when a concentration of 20.0 mM D,L glyceraldehyde in EDTA was used.

Figure 5:
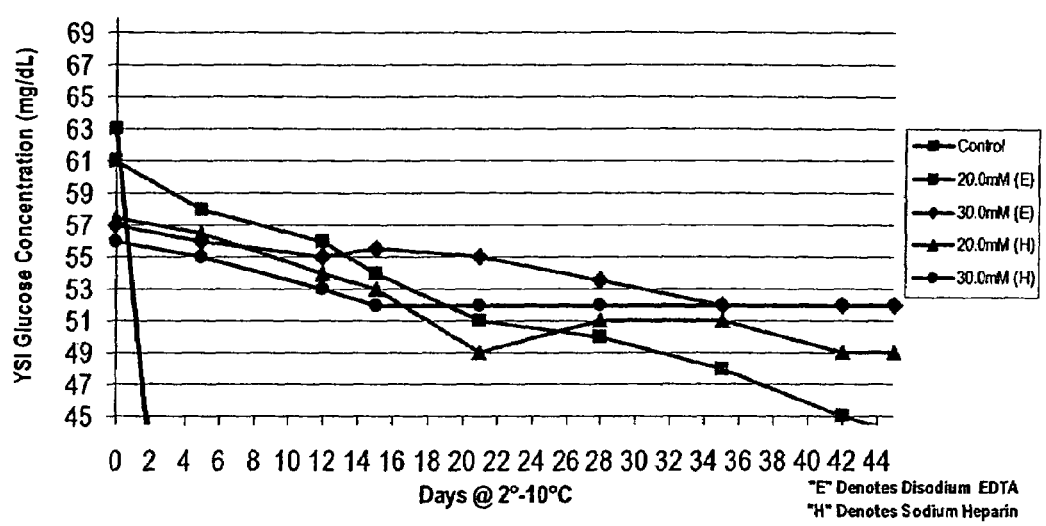
FIG. 5 illustrates the YSI 2300 (reference analyzer) glucose concentration (mg/dL) of blood specimens treated at various concentrations of D,L glyceraldehyde over 3 weeks at about 2° C. to about 10° C., wherein the control is an untreated blood sample.

FIG. 5 illustrates the YSI glucose concentration (mgl/dL) as a function of time, of blood specimens containing EDTA or heparin, with a mixture of D,L glyceraldehyde, at concentrations 20.0 mM, 30.0 mM, respectively. The samples were initially split into two portions. One portion was "burned down" to deplete its glucose concentration, and glyceraldehyde at the specified concentrations was added thereto. Glucose was then added back to reach approximately the level that was in the EDTA or heparin Control portion when the measurements were begun. The data was obtained over 3 weeks of real time testing at about 2° C. to about 10° C. The YSI glucose concentration was found to exhibit a less than 3.5% loss at 3 weeks when 30.0 mM D,L glyceraldehyde in EDTA was used.

EXAMPLE 2

In a particularly preferred, albeit not limiting, method of the instant invention a sample containing an analyte (glucose) was collected into a vacuum, microfuge tube or other container known in the art. The experimental procedural was as follows:

RBC Treatment w/Glyceraldehyde & Subsequent Removal

1) Employ fresh whole blood collected in standard anticoagulant (i.e. EDTA, heparin, sodium citrate) from a healthy adult population. Alternative blood sources may include bovine, avian, porcine, equine, goat, or alligator.
2) Allow sufficient time for the natural enzymatic breakdown of glucose to occur (i.e. glycolysis). Deplete glucose concentration to less than about 20 mg/dl. Preferred storage at 2°-30° C.
3) Separate RBC cellular component from plasma fraction via gravity settling and or centrifugation. If desired, the removed plasma fraction may be retained for reintroduction.
4) Wash RBC cellular component with isotonic phosphate buffered saline solution (3×). Exchange diluent via centrifugation is preferred (15 minutes @ 1500 rpm (650×g).
5) Adjust RBC concentration to approximately $4.0 \times 10^6/mm^3 \pm 0.25 \times 10^6/mm^3$. An acceptable operating range is from about $0.05 \times 0 \times 10^6/mm^3$ up to $10.0 \times 10^6/mm^3$
6) Combine equal volumes of the RBC cellular component with isotonic phosphate buffer saline containing approximately 70 mM glyceraldehyde (chemically, glyceraldehyde is 2,3-dihydroxypropanal in the DL, D or L form). Final glyceraldehyde concentration is preferably from about 20 mM to 200 mM. Alternative aldehydes may include benzaldehyde, hydroxypyruvaldehyde, acetaldehyde and glycolaldehyde, or combinations thereof.
7) Incubate cells @ about 2°-10° C. for a period of about 72 hours. Total incubation time is preferably from about 2 hours to about 120 hours.
8) Following completion of the specified exposure time, wash RBC cellular component back into isotonic phosphate buffered saline (3×). Exchange diluent via centrifugation is preferred (15 minutes @ 1500 rpm).
9) Resuspend Glyceraldehyde treated RBC with fresh plasma, e.g. fresh plasma retained in step #3. Target a final RBC count of $3.0-5.0 \times 10^6/mm^3$. Acceptable operating ranges are from about $0.05 \times 0 \times 10^6/mm^3$ to about $10.0 \times 10^6/mm^3$.
10) Adjust the glucose to a concentration preferably between about 20 mg/dl and 1000 mg/dl.

The initial concentration of glucose in the sample is not critical, and normally is from about 50 to about 110 mg/dL.

The anticoagulant agent may be added simultaneously, or sequentially, to the sample to form the desired suspension. Alternative means of separating the cellular components of the tissue sample, (i.e. RBCs, WBCs) from the proteineous component (i.e. plasma) may include any means known in the art, e.g. gravity settling, centrifugation, sonication, vortexing, etc.

If necessary, the proteineous component can be stored at any appropriate temperature. For example, the plasma may be incubated at 2 to 30° C.

The separated cellular component can be washed with any suitable buffered solution known in the art, a non-limiting example of which is isotonic phosphate buffered saline solution.

The glucose concentration adjusted (glycolyzed) cellular component is treated with a glycolytic inhibitor solution. The glycolytic inhibitor solution may comprise an equal volume of the appropriate buffered saline solution and at least one non-cross linking aldehyde, at about 20 to about 200 mM. In one illustrative embodiment, the non-cross linking aldehyde is about 70 mM of glyceraldehyde.

Non-limiting illustrative examples of other anti-glycolytic inhibitors may include at least one member selected from the group consisting of glyceraldehyde, benzaldehyde, hydroxypruvaldehyde, acetaldehyde, and glycolaldehyde and the like, including various combinations, known racemic mixtures or derivatives thereof.

The separated cellular components are incubated for a predetermined period of time to allow for adequate reaction with the non-cross linking aldehyde, preferably about 2 to 120 hours, most preferably about 72 hours.

Without limiting the scope of the present invention, the separated cellular component can be washed with any appropriate buffered solution known in the art, any desired amount of times.

The separated cellular component, which now represents a glycolyzed red blood cell component which has been treated with a glycolysis stabilizing effective amount of at least one non-crosslinking aldehyde compound may then be washed to remove residual glycolytic inhibitor. The red blood cell component may be supplied in a suspension, or in any form wherein it may act as a reconstitutable constituent for production of the simulated whole blood control product.

The cellular component is then resuspended in the previously separated proteineous component, or alternatively in an equivalent substitute therefore, resulting in the formation of a simulated whole blood glucose control product.

The final concentration of the cellular component being about $0.05 \times 10^6/mm^3$ to about $10.0 \times 10^6/mm^3$ the, with an operating range of 3.0 to $5.0 \times 10^6/mm^3$, preferred.

Lastly, the analyte (i.e. glucose) concentration of the treated suspension is adjusted to at least one predetermined concentration, from about 20 mg/dL to about 1000 mg/dL; preferably within the range of about 50 mg/dL to about 200 mg/dL. The particular concentration selected will remain essentially stable for a period of time sufficient for accurate measurement and calibration of a glucose measuring instrument. In a particularly preferred embodiment, the control product exhibits less than about a 5% matrix effect.

Alternative concentrations used to calibrate glucose measuring devices obvious to one of ordinary skill in the art may be used. Preferably, the amount of glucose added produces less than 1% dilution of sample.

Additionally, it has been found that addition of one or more antimicrobial substances such as doxycycline, tetracycline, minocycline or the like is effective for enhancing long-term product stability, e.g. preventing or retarding red blood cell hemolysis for a period of greater than about 40 days. The anti-microbial and/or anti-hemolytic effect of these substances upon red blood cells has yielded long-term (greater than 40 days) stability enhancement of the instant whole blood glucose controller. Effective amounts of the stability enhancement substance are within the range of at least about 5-10 mg/dL; although higher ranges are also efficacious in enhancing stability.

Figure 6:
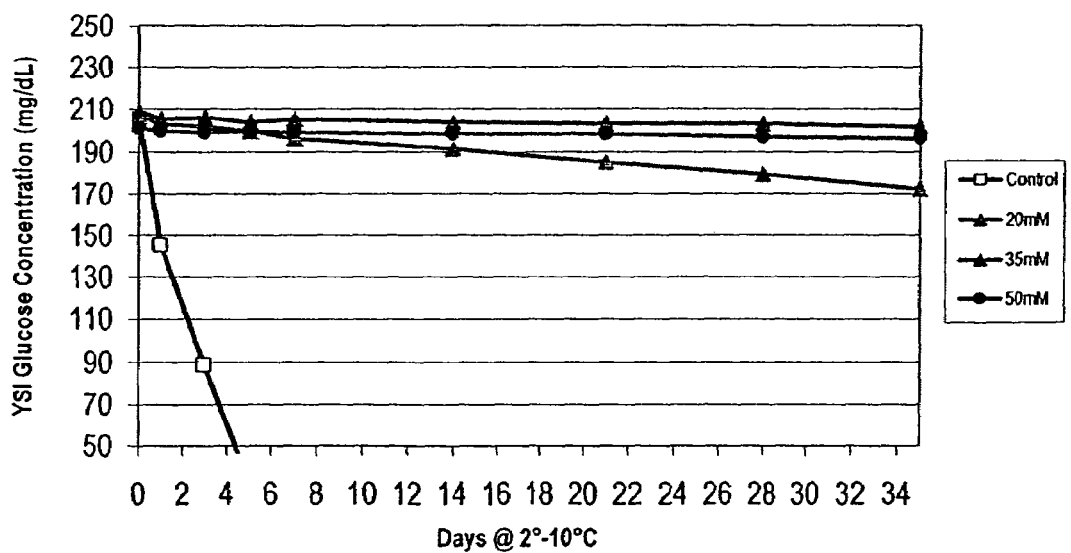
FIG. 6 illustrates the YSI 2300 (reference analyzer) glucose concentration (mg/dL) of blood specimens at various concentrations of D,L glyceraldehyde respectively over 4 weeks at about 2° C. to about 10° C., wherein the control is untreated blood sample. Red blood cells were treated, washed and recombined with plasma and glucose.

FIG. 6 illustrates RBCs treated with 20, 35, and 50 mM D,L glyceraldehyde (with 35 mM being a preferred embodiment) for 72 hours at 2 to 10° C., resulting in less than a 5% loss in glucose recovery after 34 days. The control is an untreated blood sample.

In one illustrative albeit non-limiting embodiment, the calibrator and/or control of the instant invention can be included as part of a glucose control and/or calibrator kit for use by proficiency program administrators, quality control technicians, or other persons involved in the manufacturing of glucose monitoring instrumentation. The kit including at least one source containing pre-treated glucose stabilized cellular components in combination with at least one non-cross linking aldehyde and glucose, to form aliquots and instructions for combining with plasma to create a control and/or calibrator at desired glucose concentrations. The sources of the non-cross linking aldehyde, plasma and glucose can be provided to the analyzer manufacturer in prepackaged, sealed containers or any other means known in the art.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. Any compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for preparing a whole blood calibrator/control for calibrating glucose measuring systems over an extended period of time comprising:
    supplying a whole blood sample including a cellular component and a plasma component;
    forming a whole blood suspension by addition of an anti-coagulant to said whole blood sample and metabolizing said suspension to a glucose concentration of less than about 20 mg/dL;
    treating said suspension to separate said plasma from said cellular component to form a concentrated cellular component;
    combining said concentrated cellular component with a predetermined amount of a non-crosslinking glycolytic inhibitor solution, to form a treated cellular dilution;
    incubating said treated cellular dilution whereby a further reduction in glucose concentration is obtained;
    washing said treated cellular dilution with at least one buffer solution effective to substantially remove said glycolytic inhibitor solution;
    preparing a stable whole blood suspension by intermixing said treated and washed cellular dilution and plasma in amounts effective to form a stable reconstituted whole blood sample; and
    formulating said stable reconstituted whole blood sample to contain a particular final glucose concentration;
    whereby said particular final glucose concentration remains substantially constant over time, thereby providing a stable glucose control/calibrator for use in glucose measuring systems.

2. The process of claim 1 wherein said treating step utilizes a separation step selected from the group consisting of sonicating, vortexing, gravity settling, and centrifugation.

3. The process of claim 1 wherein said treating step includes adjusting said cellular component concentration to about $0.05 \times 10^6/mm^3$ to $10.0 \times 10^6/mm^3$.

4. The process of claim 3 wherein said cellular component concentration is about $4.0 \times 10^6/mm^3$.

5. The process of claim 1 wherein said buffer solution comprises an isotonic phosphate buffered saline solution.

6. The process of claim 1 wherein said anticoagulant is at least one member selected from the group consisting of an oxalate, EDTA, citrate, heparin and combinations thereof.

7. The process of claim 1 wherein said non-crosslinking glycolytic inhibitor solution comprises at least one aldehyde.

8. The process of claim 7 wherein said non-cross linking aldehyde is within a concentration range of greater than 20 mM to about 200 mM.

9. The process of claim 8 wherein said non-cross linking aldehyde is selected from the group consisting of: glyceraldehyde, benzaldehyde, hydroxypyruvaldehyde, acetaldehyde, and glycolaldehyde or combinations thereof.

10. The process of claim 8 wherein said aldehyde is a racemic mixture of D, L-glyceraldehyde stereoisomers.

11. The process of claim 8 wherein said aldehyde is a D-glyceraldehyde stereoisomer.

12. The process of claim 8 wherein said aldehyde is a L-glyceraldehyde stereoisomer.

13. The process of claim 7 wherein said non-crosslinking glycolytic inhibitor solution further contains an isotonic phosphate buffered saline solution.

14. The process of claim 1 wherein said formulating of a stable reconstituted whole blood sample further includes adjusting the treated cellular dilution to within a concentration range of about $0.05\times10^6/mm^3$ to about $10.0\times10^6/mm^3$.

15. The process of claim 14 wherein said treated cellular dilution concentration is about $3.0\times10^6/mm^3$ to about $5.0\times10^6/mm^3$.

16. The process of claim 1 wherein said formulating step further includes adjusting said final glucose concentration within a concentration range of about 20 mg/dL to about 1000 mg/dL.

17. The process of claim 1 wherein said combining step comprises adding equal volumes of said concentrated cellular component and said glycolytic inhibitor solution.

18. The process of claim 1 wherein said incubation step provides incubation of said treated cellular dilution for from about 2 to about 120 hours.

19. A process in accordance with claim 1 further including the addition of a long term stability enhancing effective amount of at least one substance selected from the group consisting of doxycycline, tetracycline and minocycline.

20. The process in accordance with claim 19 wherein said long term stability enhancing effective amount is within the range of about 5 mg/dL -10 mg/dL.

21. A glucose control product for determining accuracy and reproducibility of operation of a glucose measuring instrument comprising:
   a glycolyzed red blood cell component which has been firstly metabolized to a glucose concentration of less than about 20 mg/dL, secondly treated with a glycolysis stabilizing effective amount of at least one non-crosslinking aldehyde compound and thirdly, further glycolyzed to a stable glucose concentration while being incubated with the at least one non-crosslinking aldehyde compound; said red blood cell component present in an amount sufficient to provide a red blood cell count, when resuspended in fresh plasma, in a range of about $0.05\times0\times10^6/mm^3$ to about $10.0\times10^6/mm^3$; and
   fresh plasma in an amount effective for resuspending said red blood cell component to a desired concentration, thereby forming a simulated whole blood glucose control product;
   whereby said simulated whole blood glucose control product is effective to maintain a particular and essentially stable glucose concentration over a period of time extending over a time period of several weeks for accurate measurement and calibration of a glucose measuring instrument.

22. The glucose control product of claim 21 wherein said red blood cell count is about $4.0\times10^6/mm^3$.

23. The glucose control product of claim 21, wherein said non-cross linking aldehyde is selected from the group consisting of: glyceraldehyde, benzaldehyde, hydroxypyruvaldehyde, acetaldehyde, and glycolaldehyde or combinations thereof.

24. The glucose control product of claim 21 wherein said non-cross linking aldehyde compound is within a concentration range of about 20 mM to about 200 mM.

25. The glucose control product of claim 21 wherein said aldehyde is a racemic mixture of D, L-glyceraldehyde stereoisomers.

26. The glucose control product of claim 21 wherein said aldehyde is a D-glyceraldehyde stereoisomer.

27. The glucose control product of claim 21 wherein said aldehyde is a L-glyceraldehyde stereoisomer.

28. The glucose control product of claim 21 wherein said particular and essentially stable glucose concentration is within the range of about 50 mg/dL to about 200 mg/dL.

29. The glucose control product of claim 21, wherein said red blood cell component further contains an isotonic suspension medium.

30. The glucose control product of claim 21, wherein said simulated whole blood glucose control product exhibits less than about a 5% matrix effect.

31. A product in accordance with claim 21 further including a long term stability enhancing effective amount of at least one substance selected from the group consisting of doxycycline, tetracycline and minocycline.

32. The product in accordance with claim 31 wherein said long term stability enhancing effective amount is within the range of about 5 mg/dL -10 mg/dL.

* * * * *